United States Patent
Swahn

[11] Patent Number: 5,710,139
[45] Date of Patent: Jan. 20, 1998

[54] HETEROCYCLIC COMPOUNDS

[75] Inventor: Britt-Marie Swahn, Södertälje, Sweden

[73] Assignee: Astra AB, Sweden

[21] Appl. No.: 381,868

[22] PCT Filed: Dec. 16, 1994

[86] PCT No.: PCT/SE94/01211

§ 371 Date: Feb. 7, 1995

§ 102(e) Date: Feb. 7, 1995

[87] PCT Pub. No.: WO95/17410

PCT Pub. Date: Jun. 29, 1995

[30] Foreign Application Priority Data

Dec. 22, 1993 [SE] Sweden .................. 9304269
Mar. 23, 1994 [SE] Sweden .................. 9400968
Jun. 16, 1994 [SE] Sweden .................. 9402122

[51] Int. Cl.$^6$ .................. A61K 31/695; C07F 9/60
[52] U.S. Cl. .................. 814/82; 546/23
[58] Field of Search .................. 546/23; 514/82

[56] References Cited

U.S. PATENT DOCUMENTS

| | | | |
|---|---|---|---|
| 5,118,675 | 6/1992 | Jirkovsky et al. | 514/80 |
| 5,124,319 | 6/1992 | Baudy et al. | 514/80 |
| 5,217,963 | 6/1993 | Hutchison et al. | 514/82 |

OTHER PUBLICATIONS

Baudy, Reinhardt B. et al. "Potent Quinoxaline–Spaced Phosphono α-Amino Acids of the AP–6 Type as Competitive NMDA Antagonists: Synthesis and Biological Evaluation," *J. Med. Chem.* 36:331–342 (1993).

Bigge, Christopher F. et al., "Exploration of Phenyl–Spaced 2–Amino–(5–9)–phosphonoalkanoic Acids as Competitive N–Methyl–D–aspartic Acid Antagonists," *J. Med. Chem.* 32:1580–1590 (1989).

Boast, Carl A. et al., "The N–methyl–D–aspartate antagonists CGS 19755 and CPP reduce ischemic brain damage in gerbils," *Brain Res.* 442:345–348 (1988).

Cahusac, P.M.B. et al., "The Behavioural Effect of an N–Methylaspartate Receptor Antagonist Following Application to the Lumbar Spinal Cord of Conscious Rats," *Neuropharmacology* 23:719–724 (1984).

Lehmann, J. et al., "CGS 19755, a Selective and Competitive N–Methyl–D–Aspartate–Type Excitatory Amino Acid Receptor Antagonist," *J. Pharmacol. Exp. Therap.* 246:65–75 (1988).

*Primary Examiner*—Robert T. Bond
*Attorney, Agent, or Firm*—Michael A. Sanzo; Vinson & Elkins

[57] ABSTRACT

Compounds of the formula I,

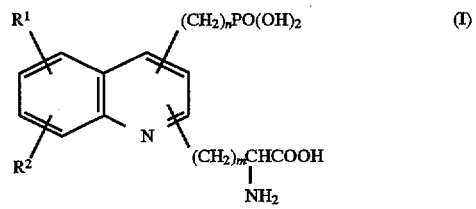

are NMDA antagonists and useful in the treatment and prevention of nervous system related pathological conditions resulting from overstimulation by excitatory amino acids. Methods for their preparation and pharmaceutical compositions containing them are also comprised according to the invention.

43 Claims, No Drawings

HETEROCYCLIC COMPOUNDS

CROSS REFERENCE TO RELATED APPLICATIONS

This is a 371 of international application PCT/SE94/01211 with an international filing date of Dec. 16, 1994, claiming priority to Swedish applications 93 04 269-5 (filed Dec. 22, 1993); 94 00 968-5 (filed Mar. 23, 1994) and 94 02 122-7 (filed Jun. 16, 1994).

FIELD OF THE INVENTION

The present invention relates to new quinoline compounds, to methods for their preparation, their use, and pharmaceutical compositions thereof. The compounds are antagonists of N-methyl-D-aspartate (NMDA) receptors and are useful in the treatment of disorders known to be responsive to blockade of the NMDA excitatory amino acid receptor. Accordingly they are especially useful in the treatment of disorders such as pain, anxiety, and cerebral ischemia and as an anaesthetic.

BACKGROUND OF THE INVENTION

The endogenous acidic amino acids, L-glutamate and L-aspartate, have been established as major excitatory neurotransmitters. The action of these excitatory amino acids is mediated by several distinct receptor subtypes of which one is the N-methyl-D-aspartate (NMDA) receptor. Excessive activation of the NMDA receptor complex is implicated in a number of neuropathological conditions and hence antagonists of this receptor complex have a potential for providing new therapeutic agents. In animal models of human disorders it has been shown that certain known NMDA antagonists have anticonvulsant activity cf. e.g. Lehmann et al. J. Pharmacol. Exp. Therap., 246, 65 (1988). This implicates the usefulness of NMDA antagonists as antiepileptic agents. Known NMDA antagonists also give protection against neuronal cell death caused by excessive stimulation cf. Boast et al. Brain Res., 442, 345 (1982). Hence, these agents may be used in the treatment of ischemic and hypoxic conditions and also of neurodegenerative disorders e.g. Alzheimer's disease. By intrathecal injection known NMDA antagonists have exhibited analgetic activity cf. Cahusac et al. Neuropharmacology, 23, 719 (1984). The antagonists may also be beneficial in the treatment of migraine, anxiety, hearing loss, motor neuron diseases, trauma from infections and illness linked to lutenizing hormone secretion. NMDA antagonists with an aryl-spaced phosphono α-amino acid structure have been described in e.g. J. Med. Chem., 32, 1580 (1989) and in J. Med. Chem., 36, 331 (1993).

OUTLINE OF THE INVENTION

The present invention is concerned with a group of novel NMDA antagonists, methods to prepare them, pharmaceutical compositions containing them and therapeutic use of the antagonists to prevent and/or relieve the physiological effects induced by overstimulation of excitatory amino acid receptors of the nervous system.

The novel compounds of the invention exhibit the following structural formula I

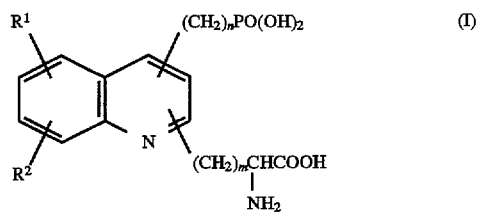

in which m is 0,1 or 2; n is 1,2 or 3; and $R^1$ and $R^2$ are, independently and being the same or different, hydrogen, $C_1$–$C_7$ alkyl, $C_2$–$C_7$ alkenyl, $C_4$–$C_7$ alkadienyl, $C_6$ aryl, $C_6$ aryl-$C_1$–$C_7$ alkyl, $C_1$–$C_7$ alkoxy, $C_1$–$C_7$ alkanoyl, $C_1$–$C_7$ alkanoyloxy, $C_6$ aroyl, $C_6$ aroyloxy, $C_6$ aryl-$C_1$–$C_7$ alkanoyl, $C_1$–$C_7$ alkoxycarbonyl, $C_6$ aryl-$C_1$–$C_7$ alkoxycarbonyl, $C_1$–$C_7$ alkylthio, trifluoromethyl, trifluoromethoxy, $C_1$–$C_7$ alkylsulfonyl-amino, $C_1$–$C_7$ alkylamino, $C_1$–$C_7$ alkanoylamino, nitro, halogen, or $R_1$ and $R_2$ are taken together, $C_1$–$C_7$ alkylene, $C_2$–$C_7$ alkenylene or $C_4$–$C_7$ alkadienylene; and the pharmaceutically acceptable esters and salts, including hydrates, of compounds according to the formula (I).

Preferred compounds of the present invention are compounds according to the formula (II)

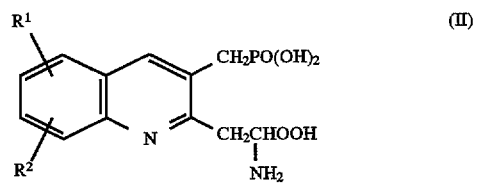

wherein $R^1$ and $R^2$ are as defined above.

The compounds of the invention are α-amino acid derivatives and thus the compounds of the invention include not only the individual enantiomers, but mixtures of enantiomers, including racemic mixtures. The R-isomer is the preferred isomeric form.

The general definitions used herein have the following meaning in the context of the invention.

When referring to a hydrocarbon moiety and hereinafter in connection with organic groups, we define such with up to and including 7 carbon atoms, more preferably up to and including 4 carbon atoms.

Preferred alkyl groups according to the invention are $C_1$–$C_4$ alkyl, represented by for example methyl, ethyl, propyl or butyl. Also within the scope are branched alkyl groups, represented by for example isopropyl. Unless otherwise indicated, cycloalkyl groups may be used in place of alkyl groups wherever mentioned herein.

When $R^1$ and $R^2$ are taken together, preferred alkylene groups according to the invention are $C_2$–$C_6$ alkylene represented by for example ethylene, propylene or butylene.

Preferred alkenyl groups are $C_2$–$C_4$ alkenyl.

Preferred alkadienyl groups are $C_4$–$C_6$ alkadienyl.

When $R^1$ and $R^2$ are taken together, preferred alkenylene groups according to the invention are $C_2$–$C_6$ alkenylene, represented by for example butenylene.

When $R^1$ and $R^2$ are taken together, preferred alkadienylene groups according to the invention are $C_4$–$C_6$ alkadienylene, represented by for example butadienylene.

Preferred $C_6$ aryl groups according to the invention are phenyl or substituted phenyl. The term "substituted phenyl" refers to phenyls having one to three substituents selected from $C_1$–$C_7$ alkyl, $C_1$–$C_7$ alkoxy, trifluoromethyl and halogen. A pyridyl, particularly 3-pyridyl, may be used in place of a $C_6$ aryl group.

Preferred $C_6$ aryl-lower alkyl groups according to the invention are $C_6$ aryl-$C_1$-$C_4$-alkyl, $C_6$ aryl having the meaning as defined above, advantageously benzyl or 2-phenylethyl.

Preferred alkoxy groups according to the invention are $C_1$-$C_4$ alkoxy, represented by for example, ethoxy, propoxy or methoxy.

Preferred alkanoyl groups according to the invention are $C_2$-$C_7$ alkanoyl, advantageously acetyl, propionyl, n-butyryl, isobutyryl or pivaloyl.

Preferrred alkanoyloxy groups according to the invention are $C_2$-$C_5$ alkanoyloxy advantageously acetoxy, propionyloxy, n- or i-butyryloxy or pivaloyloxy.

$C_6$ aroyl represents $C_6$-arylcarbonyl. Preferred aroyl groups according to the invention are benzoyl or benzoyl substituted by one to three substituents selected from $C_1$-$C_7$ alkyl, $C_1$-$C_7$ alkoxy, trifluoromethyl and halogen; or pyridylcarbonyl, particularly nicotinyl.

Preferred $C_6$ aroyloxy groups according to the invention are benzoyloxy, benzoyloxy substituted on the phenyl ring by $C_1$-$C_7$ alkyl, halogen or $C_1$-$C_7$ alkoxy; or nicotinoyloxy.

Halogen is preferably fluorine and chlorine, but may also represent bromine or iodine.

Preferred $C_6$ aryl-alkanoyl groups according to the invention are $C_6$ aryl-$C_1$-$C_4$-alkanoyl, advantageously phenylacetyl or 3-phenylpropionyl.

Preferred alkoxycarbonyl groups according to the invention are $C_1$-$C_4$ alkoxycarbonyl, i.e. containing 1–4 carbon atoms in the alkoxy portion, represented by for example: methoxycarbonyl, propoxycarbonyl, isopropoxycarbonyl or ethoxycarbonyl.

$C_6$ aryl-$C_1$-$C_7$-alkoxycarbonyl represents preferably benzyloxycarbonyl.

A pharmaceutical acceptable ester within the context of the present invention represent an ester of a compound of the invention having a carboxy group, preferably a carboxylic acid prodrug ester that may be convertible under physiological conditions to the corresponding free carboxylic acid. Most preferred prodrug esters are the $C_1$-$C_7$ alkyl, $C_6$ aryl-$C_1$-$C_7$ alkyl, $C_1$-$C_7$ alkanoyloxymethyl, $C_1$-$C_7$ alkylamino-straight chain $C_2$-$C_4$-alkyl esters for example 2-diethylaminoethyl.

The pharmaceutically acceptable salts are the alkali metal salts (sodium or potassium), the alkaline earth metal salts (calcium or magnesium), or ammonium salts derived from ammonia or from pharmaceutically acceptable organic amines, for example $C_1$-$C_7$ alkylamine, cyclohexylamine, triethanolamine, ethylenediamine or tris-(hydroxymethyl)-aminomethane. The compounds of the invention which are basic amines form acid addition salts of preferably pharmaceutically acceptable inorganic or organic acids for example hydrohalic, sulfuric, phosphoric acid or aliphatic or aromatic carboxylic or sulfonic acid, for example acetic, succinic, lactic, malic, tartaric, citric, ascorbic, nicotinic, methanesulfonic, p-toluensulfonic or naphthalenesulfonic acid.

The most preferred compounds according to the invention known at present are (R)-α-Amino-6,7-dimethyl-3-(phosphonomethyl)-2-quinolinepropanoic acid;

(R)-α-Amino-6,7-dichloro-3-(phosphonomethyl)-2-quinolinepropanoic acid; and (R)-α-Amino-6,7-diethyl-3-(phosphonomethyl)-2-quinolinepropanoic acid.

Preparations

The compounds of the present invention can be prepared by methods known in the art using readily available or readily prepared starting materials, for example several synthetic routes depending on the substituents of the quinoline starting material, are listed in the following. The substituted quinoline (III), which is a starting compound

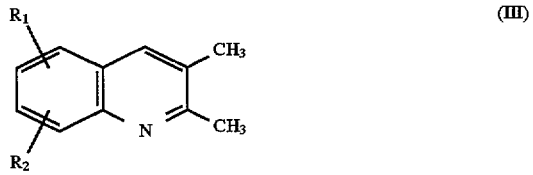

(III)

can be prepared by the Doebner-von Miller variation of the Skraup quinoline synthesis, that is from a suitably substituted or unsubstituted aniline and trans-2-methyl butenal. After brominating with N-bromosuccinimide the bromomethyl group is reacted with a trialkyl phosphite under Arbuzov reaction conditions. After a second bromination with N-bromosuccinimide the bromomethyl group is used to C-alkylate a dialkyl acetamidomalonate in the presence of an alkali metal alkoxide. Alternatively alkylation may be accomplished with a N-benzylidene glycine ester in the presence of an alkali metal alkoxide or under phase-transfer conditions using a chiral phase-transfer catalyst yielding an enantiomerically pure product. The compounds that appear as racemic mixtures can be readily resolved into their pure enantiomers by conventional means. The compounds of the invention are then obtained by removal of the protecting groups.

The substituted quinoline (IV)

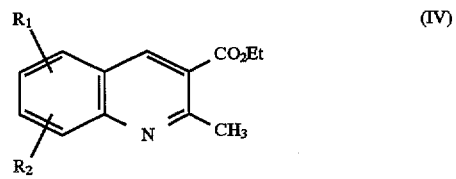

(IV)

can be prepared by a modified Friedländer quinoline synthesis, that is by condensing a suitably substituted or unsubstituted o-nitro benzaldehyde with ethyl acetoacetate and subsequent reduction of the nitro group. After bromination with N-bromosuccinimide the bromomethyl group is used to C-alkylate a dialkyl acetamidomalonate in the presence of an alkali metal alkoxide. Alternatively alkylation may be accomplished with a N-benzylidene glycine ester in the presence of an alkali metal alkoxide or under phase-transfer conditions using a chiral phase-transfer catalyst yielding an enantiomerically pure product. The ethyl 3-quinolincarboxylate can then directly or indirectly be reduced to a hydroxymethyl group. After bromination with phosphorus tribromide the bromomethyl group is reacted with a trialkyl phosphite under Arbuzov reaction conditions yielding the desired phosphonate. The compounds that appear as racemic mixtures can be readily resolved into their pure enantiomers by conventional means. The compounds of the invention are then obtained by removal of the protecting groups.

The substituted quinoline (V)

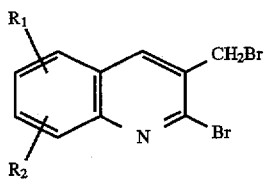

can be prepared in many ways for example, by lithiating a 2-chloroquinoline at C-3 with a lithium dialkylamide, trapping with formaldehyde and subsequent bromination with phosphorus tribromide or by first transforming a 3-carboxyethyl-2-quinolone to its 2-haloderivative subsequent reduction of the 3-carboxy group and finally bromination with phosphorus tribromide will yield the 2-bromo-3-bromomethylquinoline (V). The bromomethyl group is reacted with a trialkyl phosphite under Arbuzov reaction conditions to yield the desired phosphonate. The 2-bromoquinoline is then coupled with a 2-amidoacrylate under modified Heck reaction conditions, or reacted with a metallated β-iodoalanine. The didehydroamino acid derivative is catalytically hydrogenated using a noble metal catalyst for example Pd/C or a an asymmetric catalyst yielding an enantiomerically pure product. The compounds that appear as racemic mixtures can be readily resolved into their pure enantiomers by conventional means. The compounds of the invention are then obtained by removal of the protecting groups.

The preparation of the compounds according to the invention will now be described in detail.

A compound of the formula (VI)

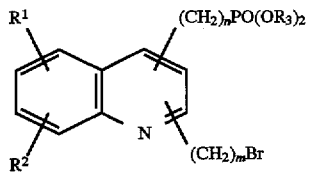

is reacted with a suitably protected glycine anion equivalent to yield a compound of the formula I with protecting groups whereafter the protecting groups are removed; or a protected compound of the formula (VII)

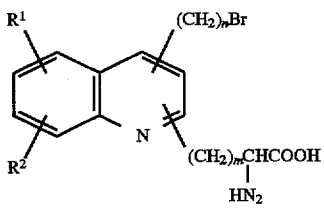

is reacted with a trialkyl phosphite, whereafter the protecting groups are removed, or a compound of the formula (VIII)

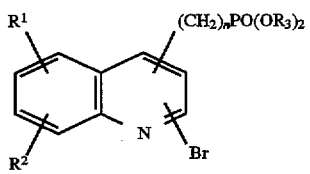

is reacted with a suitably protected 2-amidoacrylate, the compound formed is hydrogenated and the protecting groups are removed, or (VIII) is reacted with a suitably protected metallated β-iodoalanine wherafter the protecting groups are removed.

EXAMPLES

The invention will now be described in more detail with the following examples which are not to be construed as limiting the invention.

Example 1

α-Amino-3-(phosphonomethyl)-2-quinolinepropanoic acid

To a solution of 2,3-dimethylquinoline (0.50 g, 3.2 mmol) in carbon tetrachloride (40 ml) benzoyl peroxide (100 mg) and N-bromosuccinimide (1.14 g, 6.4 mmol) were added. The reaction mixture was refluxed for 4 hours, and then cooled to room temperature. The precipitate was removed by filtration and the filtrate was evaporated in vacuo. The residue was flash chromatographed on silica gel with ethyl acetate/petroleum ether as the eluent to give 0.25 g of 3-bromomethyl-2-methylquinoline.

A mixture of the obtained 3-bromomethyl-2-methylquinoline (0.25 g, 1.0 mmol) and trimethyl phosphite (0.4 ml, 3.2 mmol) was refluxed in toluene (10 ml) for 16 hours. The reaction mixture was then concentrated in vacuo and the residue was flash chromatographed on silica gel. Elution with ethyl acetate afforded 0.28 g of 3-(dimethylphosphonomethyl)-2-methylquinoline.

A solution of the obtained 3-(dimethylphosphonomethyl)-2-methylquinoline (0.28 g, 1.0 mmol) in carbon tetrachloride (20 ml) was treated with benzoylperoxide (50 mg) followed by N-bromosuccinimide (0.20 g, 1.1 mmol). The reaction mixture was refluxed for 4 hours, filtered and concentrated in vacuo. The residue was flash chromatographed on silica gel with ethyl acetate as the eluent to give 0.21 g of 2-bromomethyl-3-(dimethylphosphonomethyl)quinoline.

To a mixture of sodium (15 mg, 0.65 mmol) in ethanol (5 ml) diethyl acetamidomalonate (0.133 g, 0.61 mmol) was added. After stirring for 15 minutes 2-bromomethyl-3-(dimethylphosphonomethyl)quinoline (0.21 g, 0.61 mmol) dissolved in ethanol (5 ml) was added. The reaction mixture was stirred under dry nitrogen at room temperature for 3 hours. Ethyl acetate (25 ml) and water (5 ml) were added to the reaction mixture. The organic layer was separated and the water layer was washed with ethyl acetate (10 ml). The combined organic extracts were dried over sodium sulphate, filtered and evaporated in vacuo. The residue was flash chromatographed on silica gel. Elution with ethyl acetate afforded 0.11 g of α-acetylamino-(3-dimethylphosphonomethyl)-2-quinolinepropandioic acid diethyl ester.

The intermediate acetylamino derivative (0.11 g, 0.23 mmol) was refluxed in 6N hydrochloric acid (10 ml) for 3 hours. The mixture was concentrated in vacuo and then eluted through Dowex 50W*8H first with water and then with 1M $NH_3$ to afford 50 mg of α-amino-3-(phosphonomethyl)-2-quinolinepropanoic acid ammonium salt. $^1$H NMR ($D_2O$, 400 MHz): δ 3.30 (d, 2H, $CH_2$—P), 3.71 (d, 2H, $CH_2$), 4.49 (m, 1H, CH), 7.4–8.2 (m, 5H, ArH).

Example 2

α-Amino-2-(phosphonomethyl)-3-quinolinepropanoic acid

To a solution of 2,3-dimethylquinoline (1.0 g, 6.4 mmol) in carbon tetrachloride (60 ml) benzoyl peroxide (100 mg) and N-bromosuccinimide (2.28 g, 12.8 mmol) were added.

The reaction mixture was refluxed for 4 hours, and then cooled to room temperature. The precipitate was removed by filtration and the filtrate was evaporated in vacuo. The residue was flash chromatographed on silica gel with ethyl acetate/petroleum ether as the eluent to give 0.50 g of 2,3-di(bromomethyl)quinoline.

A mixture of 2,3-di(bromomethyl)quinoline (0.50 g, 1.4 mmol) and trimethyl phosphite (0.18 ml, 1.4 mmol) was refluxed in toluene for 4 hours. The reaction mixture was then concentrated in vacuo and the residue was flash chromatographed on silica gel. Elution with ethyl acetate afforded 0.35 g of 3-bromomethyl-2-(dimethylphosphonomethyl)quinoline.

To a mixture of sodium (20 mg, 0.90 mmol) in ethanol (5 ml) diethyl acetamidomalonate (0.19 g, 0.87 mmol) was added. After stirring for 15 minutes 3-bromomethyl-2-(dimethylphosphonomethyl)quinoline (0.30 g, 0.87 mmol) dissolved in ethanol (5 ml) was added. The reaction mixture was stirred under dry nitrogen at room temperature for 3 hours. Ethyl acetate (25 ml) and water (5 ml) were added to the reaction mixture. The organic layer was separated and the water layer was washed with ethyl acetate (10 ml). The combined organic extracts were dried over sodium sulphate, filtered and evaporated in vacuo. The residue was flash chromatographed on silica gel. Elution with ethyl acetate afforded 0.30 g of α-acetylamino-(2-dimethylphosphonomethyl)-3-quinolinepropandioic acid diethyl ester.

The intermediate acetylamino derivative (0.25 g, 0.52 mmol) was refluxed in 6N hydrochloric acid (10 ml) for 6 hours. The mixture was concentrated in vacuo and 90 mg of α-amino-2-(phosphonomethyl)-3-quinolinepropanoic acid was precipitated from water. $^1$H NMR ($D_2O$, 400 MHz): δ 3.41 (d, 2H, $CH_2$), 3.60 (d, 2H, $CH_2$—P), 4.49 (m, 1H, CH), 7.4–8.7 (m, 5H, ArH).

Example 3

α-Amino-6-chloro-3-(phosphonomethyl)-2-quinolinepropanoic acid

To a solution of 6-chloro-2,3-dimethylquinoline (2.0 g, 10.5 mmol) in carbon tetrachloride (80 ml) benzoyl peroxide (100 mg) and N-bromosuccinimide (3.7 g, 21.0 mmol) were added. The reaction mixture was refluxed for 4 hours, and then cooled to room temperature. The precipitate was removed by filtration and the filtrate was evaporated in vacuo. The residue was flash chromatographed on silica gel with ethyl acetate/petroleum ether as the eluent to give 0.90 g 3-bromomethyl-6-chloro-2-methylquinoline.

A mixture of 3-bromomethyl-6-chloro-2-methylquinoline (0.85 g, 3.0 mmol) and trimethyl phosphite (1.2 ml, 9.6 mmol) was refluxed in toluene (20 ml) for 16 hours. The reaction mixture was then concentrated in vacuo and the residue was flash chromatographed on silica gel. Elution with ethyl acetate afforded 0.90 g of 6-chloro-3-(dimethylphosphonomethyl)-2-methylquinoline.

A solution of 6-chloro-3-(dimethylphosphonomethyl)-2-methylquinoline (0.85 g, 2.7 mmol) in carbon tetrachloride (40 ml) was treated with benzoyl peroxide (100 mg) followed by N-bromosuccinimide (0.50 g, 2.8 mmol). The reaction mixture was refluxed for 4 hours, filtered and concentrated in vacuo. The residue was flash chromatographed on silica gel with ethyl acetate as the eluent to give 0.75 g of 2-bromomethyl-6-chloro-3-(dimethylphosphonomethyl)quinoline.

To a mixture of sodium (44 mg, 1.9 mmol) in ethanol (10 ml) diethyl acetamidomalonate (0.40 g, 1.85 mmol) was added. After stirring for 15 minutes 2-bromomethyl-6-chloro-3-(dimethylphosphonomethyl)quinoline (0.70 g, 1.85 mmol) dissolved in ethanol (10 ml) was added. The reaction mixture was stirred under dry nitrogen at room temperature for 3 hours. Ethylacetate (50 ml) and water (10 ml) were added to the reaction mixture. The organic layer was separated and the water layer was washed with ethyl acetate (20 ml). The combined organic extracts were dried over sodium sulphate, filtered and evaporated in vacuo. The residue was flash chromatographed on silica gel. Elution with ethyl acetate afforded 0.46 g of α-acetylamino-6-chloro-(3-dimethylphosphonomethyl)-2-quinolinepropandioic acid diethyl ester.

The intermediate acetylamino derivative (0.40 g, 78 mmol) was refluxed in 6N hydrochloric acid for 6 hours. The mixture was concentrated in vacuo and 150 mg of α-amino-6-chloro-3-(phosphonomethyl)-2-quinolinepropanoic acid was precipitated from water. $^1$H NMR ($D_2O$, 400 MHz): δ 3.29 (d, 2H, $CH_2$—P), 3.69 (d, 2H, $CH_2$), 4.49 (m, 1H, CH), 7.4–8.7 (m, 4H, ArH).

Example 4

(R)-α-Amino-7-ethoxy-3-(phosphonomethyl)-2-quinolinepropanoic acid

Phosphorus oxychloride (36.4 ml, 0.4 mol) was slowly added to stirred ice-cooled dimethylformamide (6.6 ml, 86 mmol). The cooling-bath was removed and N-(3-ethoxyphenyl)-3 chloropropionamide (13 g, 57 mmol) was added to the mixture which then was heated at reflux for 10 h. After cooling the mixture was poured onto crushed ice and solid sodium carbonate was added until ceasure of evolution of carbon dioxide. The mixture was extracted with toluene-EtOAc, after drying (sodium sulfate) the extract was filtered through a pad of silica gel and the solvents were evaporated giving 9.9 g of 2-chloro-3-chloromethyl-7-ethoxyquinoline (about 85% pure). Recrystallization from propyl acetate gave 6.0 g of pure material.

The product from the above reaction was allowed to react with 15 ml of triethyl phosphite at 125° C. for 15 h. The triethyl phosphite was evaporated under vacuum at 60° C. Recrystallization of the residue gave 2-chloro-3-diethylphosponomethyl-7-ethoxyquinoline.

The above phosphonate was treated for 10 h with 5 equivalents of sodium iodide in refluxing 2-butanone in the presence of 0.5 equivalents of methanesulfonic acid. The mixture was neutralized with saturated sodium hydrogen carbonate and extracted with ether. Evaporation of solvents gave 3-diethylphosphonomethyl-7-ethoxy-2-iodoquinoline which still contained about 20% of the starting chloride.

The above iodide was used in the coupling with the zinc reagent derived from BOC-protected methyl ester of D-3-iodoalanine as described in the following. The zinc reagent was generated in a mixture of toluene and N,N-dimethylacetamide essentially as described in Jackson et al., J. Org. Chem. 1992, 57, 3397. To the solution of the zinc reagent were added tri-o-tolylphosphine (0.2 equiv.), palladium chloride (0.1 equiv.) and the above iodide (0.55 equiv.) and sonication was continued for 3 h. The mixture was worked-up by partitioning between water and ethyl acetate. Evaporation of solvents gave methyl α-t-butoxycarbonylamino-3-diethylphosphonomethyl-7-ethoxy-2-quinolinepropionate in 50% yield after chromatography.

Deprotection of the amino acid was effected in refluxing 6M HCl for 6 h. Evaporation of the solvent gave a residue which was put onto an acidic ion-exchange resin and eluted with water. Collection of ninhydrin-sensitive fractions and evaporation of solvent gave (R)-α-amino-3-phosphonomethyl-7-ethoxy-2-quinolinepropanoic acid. $^{13}$C-NMR (D$_2$O plus NH$_3$ vapours): δ (ppm) 174.7, 158.7, 156.3, 146.3, 138.0, 137.9, 128.6, 122.6, 118.8, 106.2, 64.4, 54.1, 34.2, 34.0, 32.8, 13.9.

Example 5

(R)-α-Amino-6,7-dimethyl-3-(phosphonomethyl)-2-quinolinepropanoic acid

2-Chloro-3-diethylphosphonomethyl-6,7-dimethylquinoline (0.40 g, 1.17 mmol), prepared as described in Example 4 was dissolved in 2-butanone (20 ml) and treated with sodium iodide (0.39 g, 2.6 mmol) and p-toluenesulfonic acid (0.11 g, 0.58 mmol). The mixture was refluxed for 10 hours. Ethyl acetate and saturated sodium hydrogen carbonate were added. The organic phase was separated and filtered through a pad of silica gel. Evaporation of solvents gave 0.28 g of 3-diethylphosphonomethyl-6,7-dimethyl-2-iodoquinoline.

A solution of methyl (R)-α-t-butoxycarbonylamino-β-iodopropionate (0.40 g, 1.21 mmol) in dry toluene (6 ml) and dry dimethylacetamide (0.4 ml) was added to a nitrogen purged flask charged with zinc-copper couple (0.16 g, 2.43 mmol). The resulting mixture was sonicated under nitrogen for 55 minutes until no starting material remained. Palladium chloride (23 mg, 0.13 mmol) and tri-o-tolylphosphine (61 mg, 0.20 mmol) were added followed by the above prepared 2-iodoquinoline (0.28 g, 0.65 mmol) dissolved in toluene (2 ml). The mixture was sonicated one hour and then stirred at 55° C. for 3 hours. Ethyl acetate and saturated sodium hydrogen carbonate were added. The organic phase was washed with water and evaporated. Flash chromatography over silica gel gave 0.23 g of methyl (R)-α-t-butoxycarbonylamino-3-diethylphosphonomethyl-6,7-dimethyl-2-quinolinepropionate.

The above amino acid derivative (0.23 g, 0.45 mmol) was refluxed in 6N hydrochloric acid (10 ml) for 6 hours. The mixture was concentrated in vacuo and 110 mg of (R)-α-amino-6,7-dimethyl-3-(phosphonomethyl)-2-quinolinepropanoic acid was precipitated from water. $^1$H NMR (D$_2$O plus NH$_3$, 400 MHz): δ 2.28 (s, 3H, CH$_3$), 2.30 (s, 3H, CH$_3$), 3.00 (m, 2H, CH$_2$—P), 3.45 (m, 2H, CH$_2$), 4.20 (m, 1H, CH), 7.44 (s, 1H, ArH), 7.60 (s, 1H, ArH), 7.92 (d, 1H, ArH).

Example 6

(R)-α-Amino-7-chloro-3-(phosphonomethyl)-2-quinolinepropanoic acid

Methyl(R)-α-t-butoxycarbonylamino-7-chloro-3-diethylphosphonomethyl-2-quinolinepropionate (0.23 g, 0.45 mmol), prepared as described in example 5, was refluxed in 6N hydrochloric acid (10 ml) for 6 hours. The mixture was concentrated in vacuo and 100 mg of (R)-α-amino-7-chloro-3-(phosphonomethyl)-2-quinolinepropanoic acid was precipitated from water. $^1$H NMR(D$_2$O, 400 MHz): δ 3.18 (d, 2H, CH$_2$—P), 3.58 (m, 2H, CH$_2$), 4.38 (m, 1H, CH), 7.12 (d, 1H, ArH), 7.47 (d, 1H, ArH), 7.53 (s, 1H, ArH), 8.42 (d, 1H, ArH).

Example 7

α-Amino-6,7-dimethoxy-3-(phosphonomethyl)-2-quinolinepropanoic acid

A mixture of 2-nitro-4,5-dimethoxybenzaldehyde (5.28 g, 25 mmol) and Raney-nickel in THF (100 ml) was hydrogenated until three equivalents of hydrogen had been consumed. The mixture was filtered through Celite. Ethyl acetoacetate (3.2 ml, 25 mmol) and piperidine (12 drops) were added and the solution was refluxed for 4 h and concentrated. The solid residue was recrystallized from MeOH to give 3.89 g ethyl 6,7-dimethoxy-2-methylquinoline-3-carboxylic acid.

A solution of 6,7-dimethoxy-2-methylquinoline-3-carboxylic acid ethyl ester (2.83 g, 10.3 mmol) in dry THF (75 ml) was added dropwise over 20 min to a stirred, ice-cooled suspension of lithium aluminiumhydride (0.39 g, 10.3 mmol) in dry THF (50 ml). The mixture was allowed to come to room temperature over 2 h and the excess lithium aluminiumhydride was decomposed by sequential careful addition of ethyl acetate, acetone and 2M NaOH. The mixture was filtered and the white gummy material was extracted twice with acetone. The filtrate and the extracts were combined and concentrated to give 2.31 g of 6,7-dimethoxy-2-methylquinoline-3-methanol.

6,7-Dimethoxy-2-methylquinoline-3-methanol (2.31 g, 9.9 mmol) was dissolved in thionylchloride (50 ml) and refluxed for 2 h. The solution was concentrated and the residue partitioned between ethyl acetate and aqeous NaHCO$_3$. The layers were separated and the aqeous phase extracted with ethyl acetate. The combined organic phases were washed with water and brine and dried over MgSO$_4$. Evaporation of the solvent gave 2.48 g 6,7-dimethoxy-3-chloromethyl-2-methylquinoline.

A mixture of 6,7-dimethoxy-3-chloromethyl-2-methylquinoline (2.48 g, 9.9 mmol) and triethylphosphite (6 ml) was heated at 160° C. for 4 h and cooled to room temperature. Excess triethylphosphite was removed by extraction with hexane and the remaining dark oil was purified by chromatography to give 3.50 g 3-(diethylphosphonomethyl)-6,7-dimethoxy-2-methylquinoline.

SeO$_2$ (0.56 g, 5.06 mmol) was added to a solution of 3-(diethylphosphonomethyl)-6,7-dimethoxy-2-methylquinoline (1.79 g, 5.06 mmol) in dioxane (25 ml). The mixture was refluxed for 75 min, filtered and concentrated. The remaining oil was purified by chromatography to give 1.48 g 3-(diethylphosphonomethyl)-6,7-dimethoxyquinoline-2-carboxaldehyde.

A solution of N-benzyloxycarbonyl-α-(dimethylphosphonyl)glycin methyl ester (0.99 g, 3 mmol) in THF (4 ml) was added dropwise to a stirred suspension of NaH (82 mg, 3.4 mmol) in THF (2 ml) at room temperature. After the gas evolution had ceased a solution of 3-(diethylphosphonomethyl)-6,7-dimethoxyquinoline-2-carboxaldehyde (1.13 g, 3 mmol) in THF (3 ml) was added dropwise over 2 min. After 2 h the reaction was quenched with aqeous NH$_4$Cl and partitioned between ethyl acetate and water. The layers were separated and the aqeous phase extracted with ethyl acetate. The combined organic phases were washed with water and brine and dried over MgSO$_4$. Concentration gave a brown foam which was purified by chromatography to give 1.04 g α-(benzyloxycarbonylamino)-3-(diethylphosphonomethyl)-6,7-dimethoxy-2-quinolineacrylic acid methyl ester.

A mixture of α-(benzyloxycarbonylamino)-3-(diethylphosphonomethyl)-6,7-dimethoxy-2-quinolineacrylic acid methyl ester (0.14 g, 0.25 mmol) and a catalytic amount of palladium on charcoal (10%) in MeOH (10 ml) was hydrogenated at 4 bar for 20 h. Filtration and chromatographic purification gave 0.09 g α-amino-3-(diethylphosphonomethyl)-6,7-dimethoxy-2-quinolinepropanoic acid methyl ester.

α-Amino-3-(diethylphosphonomethyl)-6,7-dimethoxy-2-quinolinepropanoic acid methyl ester (0.09 g, 0.2 mmol) was refluxed in 6M HCl (15 ml) for 6 h. The mixture was concentrated and dissolved in water. After removal of some undissolved material by filtration, 38 mg of the title compound, α-amino-6,7-dimethoxy-3-(phosphonomethyl)-2-quinolinepropanoic acid was precipitated by addition of acetonitrile. $^1$H NMR(D$_2$O, 400 MHz): δ 3.22 (dd, 2H), 3.66 (m, 2H), 3.90 (s, 3H), 3.92 (s, 3H), 4.15 (m, 1H), 7.22 (s, 1H), 7.37 (s, 1H), 8.53 (s, 1H).

Example 8

(R)-α-Amino-7-methyl-3-(phosphonomethyl)-2-quinolinepropanoic acid hydrochloride To a solution of 30 ml m-toluidine in 150 ml toluene was added a solution of 25 ml of acetyl chloride in 50 ml of toluene. The reaction mixture was cooled in a +20° C. water bath giving a reaction of temperature of +50° C. at the end of the addition. The mixture was stirred at room temperature overnight, then diluted with 100 ml of toluene, washed with 200 ml of H$_2$O, 100 ml of saturated sodium bicarbonate solution and then filtered through phase separating paper and evaporated in vacuo to give 37.2 g of N-acetamido-m-toluidine as a crystalline mass.

31 ml (0.4 mol) of dry dimethylformamide was cooled in an ice/ethanol-bath, and 87 ml (0.94 mol) of phosphorous oxychloride was added during 30 minutes with mechanical stirring to give the formiminium chloride as a suspension. 20 g (0.134 mol) of powdered N-acetamido-m-toluidine was then added at 0° to +5° C. The mixture was allowed to reach room temperature over 1.5 hours and was then heated at +80° C. in a stoppered flask fitted with a reflux condenser for 3 hours. After standing at room temperature overnight the mixture was poured onto 1 l of chrushed ice and the mixture stirred for approx. 30 minutes. The precipitate was filtered off, washed with water and dried in vacuo to give 18.5 g of 2-chloro-3-formyl-7-methylquinoline.

To a stirred solution of 6.9 g (180 mmol) of sodium borohydride in 250 ml of absolute ethanol, a solution of 15 g (73 mmol) of 2-chloro-3-formyl-7-methylquinoline in 250 ml of dry tetrahydrofuran was added over 15 minutes without cooling. During the addition a slight H$_2$-evolution and a temperature rise to +28° C. was observed. The reaction mixture was stirred at room temperature for 4 hours and then 4 ml of the reaction mixture was evaporated in vacuo and the residue dissolved in ethyl acetate, extracted with saturated sodium hydrogen carbonate solution, dried over sodium sulfate and evaporated in vacuo to give a residue of 100 mg. $^1$H-NMR indicated complete conversion to the alcohol. After 5 hours the whole reaction mixture was worked up in the same way to give 14.8 g 2-chloro-3-hydroxymethyl-7-methylquinoline after evaporation.

10 ml (106 mmol) of phosphorus tribromide was cooled in an ice-bath and 6.4 g (30.8 mmol) of solid 2-chloro-3-hydroxymethyl-7-methylquinoline was added with stirring. The temperature reached +10° C. at the end of the addition and a thick suspension was formed. The cooling bath was then removed and the mixture was heated at +100° C. for 3 hours. 50 ml of toluene was added and the mixture refluxed for another 3 hours. The reaction mixture was then poured onto 200 ml of ice, the resulting mixture filtered, the toluene phase separated from the filtrate, the solids redissolved in methylene chloride, the toluene and methylene chloride solutions combined, washed with water, dried and avaporated in vacuo to give 5.9 g of 2-bromo-3-bromomethyl-7-methylquinoline as a crystalline solid. $^1$H-, $^{13}$C-NMR and MS showed the presence of 20% 2-chloro-3-bromomethyl-7-methylquinoline as an impurity which could not be removed by recrystallization.

To a solution of 4 g (12.6 mmol) of the above 2-bromo-3-bromomethyl-7-methylquinoline in 50 ml of toluene was added 4.3 ml (25 mmol) of triethyl phosphite and the mixture was refluxed for 22 hours. Evaporation in vacuo gave 5.1 g of a solid residue which was dissolved in 10 ml of toluene (slightly warmed) and diluted with hexane until turbid. The solution was decanted from a small amount of a fluffy precipitate and was then allowed to crystallize in an ice bath. The crystalline precipitate was filtered off, washed with hexane and dried in vacuo to give 3.3 g of 2-bromo-3-diethylphosphonomethyl-7-methylquinoline containing 20% of 2-chloro-3-diethylphosphonomethyl-7-methylquinoline as an impurity.

To a solution of 2.5 g (7.5 mmol) of N-t-butoxycarbonyl-3-iodo-D-alanine methyl ester in 30 ml of dry toluene and 2 ml of dry N,N-dimethylacetamide was added 900 mg of Zn(Cu) dust. The mixture was treated in an ultrasonic bath for 1 hour 50 minutes after which time TLC indicated complete conversion of the iodo-alanine derivative. A mixture of 70 mg (0.4 mmol) of PdCl$_2$ and 240 mg (0.8 mmol) of tri-o-tolylphosphine was added followed by 1.9 g (5.0 mmol) of 2-bromo-3-diethylphosphonomethyl-7-methylquinoline and sonication was continued for 3 hours at 50°–60° C. and the mixture was then allowed to stand at room temperature overnight. The reaction mixture was diluted with ethyl acetate, extracted with saturated sodium hydrogen carbonate solution, dried over sodium sulfate and evaporated to give 3.91 g of an oil. The crude product was subjected to chromatography on silica gel with ethyl acetate as an eluant to give 1.334 g of pure methyl (R)-α-t-butoxycarbonylamino-3-didiethylphosphonomethyl-7-methyl-2-quinolinepropionate.

1.27 g (2.57 mmol) of methyl (R)-α-t-butoxycarbonylamino-3-diethylphosphonomethyl-7-methyl-2-quinolinepropionate was added to 20 ml of 6M hydrochloric acid and the mixture was refluxed for 6 hours. Evaporation in vacuo gave 1.03 g of a solid which was redissolved in 5 ml of water, 5 ml of isopropyl alcohol was added and the mixture was allowed to crystallize in an ice-bath. The precipitate was filtered off and dried in vacuo to give 399 mg of α-amino-3-phosphonomethyl-7-methyl-2-quinolinepropanoic acid hydrochloride. $^{13}$C-NMR(D$_2$O): δ (ppm) 21.5, 30.7, 31.9, 32.0, 51.6, 118.1, 126.2, 127.9, 128.6, 132.4, 137.4, 140.4, 147.4, 151.4, 170.8.

Example 9

(R)-α-Amino-6,7-dichloro-3-(phosphonomethyl)-2-quinolinepropanoic acid 3,4-Dichloro-6-nitrobenzaldehyde (4.40 g, 20 mmol) was dissolved in 50% aqueous ethanol (200 ml) at 50°–60° C. and the solution was added to a solution of iron(II) sulfate heptahydrate (27.8 g, 100 mmol) in water (200 ml) at 90° C. Concentrated (25%) aqueous ammonia (50 ml) was added in several portions with intensive stirring while the temperature was kept close to the boiling point. The mixture was refluxed for 5–10 min. and cooled. The precipitate was filtered off and washed with ethanol. The filtrate was concentrated in vacuo until most of the ethanol was removed. The resulting precipitate was collected, washed with water and dried in vacuo at 40°–50° C. to give 3.3 g of 3,4-dichloro-6-aminobenzaldehyde.

3,4-Dichloro-6-aminobenzaldehyde (2.85 g, 15 mmol) was stirred with dimethylmalonate (10 ml) at 140° C. for 20 h. The mixture was diluted with ethyl ether (100 ml). The precipitate was collected, washed twice with ethyl ether and dried in vacuo to give 2.86 g of methyl 6,7-dichloro-2-hydroxyquinoline-3-carboxylate.

Methyl 6,7-dichloro-2-hydroxyquinoline-3-carboxylate (2.72 g, 10 mmol) was added in small portions to a stirred solution of DIBAL (1M in hexane, 25 ml, 25 mmol) in tetrahydrofuran (25 ml) under nitrogen at 25°–30° C. The mixture was stirred at ambient temperature for 0.5 h and then quenched with an excess of 20% HCl at 5°–10° C. The precipitate was collected and washed with water, tetrahydrofuran and ethyl ether to give 2.12 g of 6,7-dichloro-2-hydroxyquinoline-3-methanol.

A mixture of 6,7-dichloro-2-hydroxyquinoline-3-methanol (1.22 g, 5 mmol) and phosphorus oxybromide (5 g) was stirred at 110° C. for 2–3 h. After cooling it was cautiously quenched with water keeping the temperature below 50° C. The precipitate was collected and washed with water, acetonitrile and ethyl ether to give 1.66 g of 6,7-dichloro-2-bromo-3-bromomethylquinoline.

A mixture of 6,7-dichloro-2-bromo-3-bromomethylquinoline (0.74 g, 2 mmol) and trimethylphosphite (5 ml) was heated at 80°–90° C. for 2–3h. Then the excess trimethylphosphite was removed in vacuo at 70°–80° C. and the oily residue was made crystalline by treating with hexane-ethyl ether (1:1). The crystals were collected, washed with toluene and dried in vacuo to give 0.65 g of 6,7-dichloro-3-dimethylphosphonomethyl-2-bromoquinoline.

A solution of N-t-butoxycarbonyl-3-iodo-D-alanine methyl ester (0.66 g, 2 mmol) in dry benzene (3 ml) and dry dimethylacetamide (0.5 ml) was added to a zinc-copper couple (0.31 g). The resulted mixture was sonicated at 40°–45° C. under nitrogen for 2.5–3 h until no starting material remained (as judged by TLC). Tri-o-tolylphosphine (0.06 g, 0.2 mmol) and palladium chloride (0.02 g, 0.1 mmol) were added followed by a solution of 6,7-dichloro-3-dimethylphosphonomethyl-2-bromoquinoline (0.4 g, 1 mmol) in dry benzene (3 ml) and dry dimethylacetamide (0.5 ml). The resulted mixture was stirred under nitrogen at 50°–60° C. for 2.5–3 h and then allowed to cool. Water was added and the mixture was filtered through Celite, the latter was washed with ethyl acetate. The combined organic phases were separated, dried, (MgSO$_4$) and concentrated in vacuo. The residue was coevaporated several times with toluene to remove most of the dimethylacetamide and then purified on a silica gel column using 0–2% methanol in chloroform as eluent to give 0.33 g of methyl (R)-α-t-butoxycarbonylamino-6,7-dichloro-3-dimethylphosphonomethyl-2-quinolinepropionate.

Methyl (R)-α-t-butoxycarbonylamino-6,7-dichloro-3-dimethylphosphonomethyl-2-quinolinepropionate (0.26 g, 0.5 mmol) was refluxed in 6M HCl (20 ml) for 4 h. The solvent was removed in vacuo and the residue was coevaporated 3 times with acetonitrile. The resulting powder was treated with water and chloroform, filtered off and finally recrystallized from methanol to give 0.11 g of (R)-α-amino-6,7-dichloro-3-(phosphonomethyl)-2-quinolinepropanoic acid. $^1$H NMR (D$_2$O, 400 MHz): δ 3.15 (d,2H), 3.56 (dd,1H), 3.64 (dd,1H), 4.41 (m,1H), 7.91 (s,1H), 8.00 (s,1H), 8.02 (s,1H).

Example 10

(R)-α-Amino-5-chloro-3-(phosphonomethyl)-2-quinolinepropanoic acid

Following the procedure of Example 9 starting with 2-chloro-6-nitrobenzaldehyde, the title compound was prepared. $^1$H NMR (CD$_3$OD, 400 MHz): δ 3.52 (d,2H), 3.94 (m,2H), 4.76 (m,1H), 7.78 (m,1H), 8.12 (m,2H), 8.76 (d,1H).

Example 11

(R)-α-Amino-6-fluoro-3-(phosphonomethyl)-2 quinolinepropanoic acid

Following the procedure of Example 9 starting with 3-fluoro-6-nitrobenzaldehyde, the title compound was prepared. $^1$H NMR (D$_2$O, 400 MHz): δ 3.24 (d,2H), 3.71 (m,2H), 4.43 (t,1H), 7.60 (m,2H), 7.94 (m,1H), 8.61 (d,1H).

Example 12

(R)-α-Amino-6,8-dichloro-3-(phosphonomethyl)-2 quinolinepropanoic acid

Following the procedure of example 9 starting with 3,5-dichloro-6-nitrobenzaldehyde, the title compound was prepared. $^1$H NMR (D$_2$O, 400 MHz): δ 3.15 (dd,2H), 3.70 (m,2H), 4.55 (t,1H), 7.36 (s,1H), 7.44 (s,1H), 7.80 (m,1H).

Example 13

(R)-α-Amino-7-chloro-6-methyl-3-(phosphonomethyl)-quinolinepropanoic acid

3-Chloromethyl-2,7-dichloro-6-methylquinoline was prepared following the procedure of Example 4 starting with 3-chloro-N-(3-chloro-4-methylphenyl)propionamide.

3-Chloromethyl-2,7-dichloro-6-methylquinoline (3.4 g, 13 mmol) and phosphorus oxybromide (15 g) was heated to 100° C. for 4 h. The mixture was allowed to cool and then poured onto crushed ice. The resulting mixture was extracted with methylene chloride and the organic phase was washed with saturated sodium hydrogen carbonate solution, dried over MgSO$_4$ and evaporated in vacuo to yield 4.4 g of 2-bromo-3-bromomethyl-7-chloro-6-methylquinoline.

A mixture of 2-bromo-3-bromomethyl-7-chloro-6-methylquinoline (4.2 g, 12 mmol), toluene (50 ml) and triethylphosphite (4.2 ml) was refluxed for 20 h. After cooling the solution was concentrated in vacuum and the product precipitated by the addition of hexane. The crystals were filtered off, washed with hexane and dried in vacuo to give 4.5 g of 2-bromo-7-chloro-3-diethylphosphonomethyl-6-methylquinoline.

A solution of N-t-butoxycarbonyl-3-iodo-D-alanine methyl ester (0.81 g, 2.46 mmol) in dry toluene (12 ml) and dry dimethylacetamide (0.8 ml) was added to a nitrogen purged flask charged with zink-copper couple (0.32 g, 4.92 mmol). The mixture was treated in an ultrasonic bath for 1 h until no starting material remained (as judged by TLC). A mixture of PdCl$_2$ (23 mg, 0.13 mmol) and tri-o-tolylphosphine (79 mg, 0.26 mmol) was added followed by 2-bromo-7-chloro-3-diethylphosphonomethyl-6-methylquinoline (0.5 g, 1.23 mmol) and sonication was continued for 3 hours at 50°–60° C. After cooling the reaction mixture was diluted with ethyl acetate, extracted with saturated sodium hydrogen carbonate solution, dried over MgSO$_4$ and evaporated. The crude product was subjected to chromatography on silica gel with ethyl acetate as eluant to yield 0.49 g of methyl (R)-α-t-butoxycarbonylamino-7-chloro-3-diethylphosphonomethyl-6-methyl-2-quinolinepropionate.

(R)-α-t-butoxycarbonylamino-7-chloro-3-diethylphosphonomethyl-6-methyl-2-quinolinepropionate was refluxed in 6N hydrochloric acid (15 ml) for 6 hours. The mixture was concentrated in vacuo and the product was crystallized from a water-acetone mixture. The product was filtered off and dried in vacuo to yield 0.31 g of (R)-α-7-chloro-6-methyl-3-(phosphonomethyl)-2-quinolinepropanoic acid. $^1$H NMR (D$_2$O, 400 MHz): δ 2.10 (s,3H), 3.26 (d,2H), 3.63 (m,2H), 4.44 (t,1H), 7.61 (s,1H), 7.75 (s,1H), 8.53 (d,1H).

Example 14

(R)-α-Amino-6,7-diethyl-3-(phosphonomethyl)-2 quinolinepropanoic acid

Following the procedure of Example 8 starting with N-(3,4-diethylphenyl)acetamide, the title compound was prepared. $^1$H NMR (D$_2$O, 400 MHz): δ 1.10 (m,6H), 2.69 (m,4H), 3.36 (d,2H), 3.6 (d,2H), 4.54 (t,1H), 7.73 (s,1H), 7.77 (s,1H), 8.69 (s,1H).

Example 15

(S)-α-Amino-6,7-dimethyl-3-(phosphonomethyl)-2 quinolinepropanoic acid

Following the procedure of Example 13 starting with 3-chloro-N-(3,4-dimethylphenyl)propionamide and using N-t-butoxycarbonyl-3-iodo-L-alanine methyl ester in the coupling reaction, the title compound was prepared. $^1$H NMR (D$_2$O, 400 MHz): δ 2.10 (s, 3H), 2.12 (s,3H), 3.23 (d,2H), 3.62 (d,2H), 4.45 (t,1H), 7.58 (s,1H), 7.62 (s,1H), 8.49 (d,1H).

Example 16

Ethyl (R)-α-amino-6,7-dimethyl-3-(phosphonomethyl)-2 quinolinepropionate

Following the procedure of Example 13 starting with 3-chloro-N-(3,4-dimethylphenyl)propionamide, the (R)-α-amino-6,7-dimethyl-3-(phosphonomethyl)-2 quinolinepropanoic acid was prepared. This amino acid (0.15 g, 0.44 mmol) was refluxed in ethanol (15 ml) saturated with hydrochloric acid for 16 hours. The solvent was removed in vacuo and the product was recrystallized in ethanol-acetone mixture. The product was filtered off and dried in vacuo to give 0.15 g of ethyl (R)-α-amino-6,7-dimethyl-3-(phosphonomethyl)-2-quinolinepropionate. $^1$H NMR (CD$_3$OD, 400 MHz): δ 1.11 (t,3H), 2.48 (s,3H), 2.52 (s,3H), 3.44 (d,2H), 3.85 (d,2h) 4.24 (q,2H), 4.75 (t,1H), 7.76 (s,1H), 7.90 (s,1H), 8.42 (d,1H).

Pharmaceutical Preparations

Pharmaceutical preparations containing a compound of the formula I are made according to known methods. When the compounds are used as NMDA-antagonists a compound according to the invention is dissolved in a liquid diluent suitable for injection. It is especially preferred to dissolve the compounds in isotonic sodium chloride solution. When the compounds are used according to the invention it is also possible to administer them in form of an oral or rectal preparation such as tablets, capsules or suppositories. To produce pharmaceutical preparations containing a compound of the formula I in the form of dosage units for oral administration the selected compound may be mixed with a solid excipient, e.g. lactose or cellulose derivatives, a binder such as gelatine, and a lubricant such as magnesium stearate, and then compressed into tablets. Dosage units for rectal application can be solutions or suspensions or can be prepared in the form of suppositories. Liquid preparations for oral application may be in the form of syrups or suspensions e.g. solutions containing from about 0.2% to about 20% by weight of the active substance herein described. Solutions for parenteral applications by injection can be prepared in an aqueous solution of a water-soluble pharmaceutically acceptable salt of the active substance. These solutions may optionally contain stabilizing agents and/or buffering agents and may conveniently be provided in various dosage unit ampoules. Suitable unit dosages of the compounds of the invention in therapeutical treatment of human adults are from 10 to 800 mg at peroral administration and 0.1 to 100 μg at intrathecal administration.

Biological Evaluation

The compounds of the invention exhibit valuable pharmacological properties, e.g. blocking the NMDA excitatory amino acid receptor in mammals. Thus, these novel compounds are useful in the treatment of ischemic conditions; stroke; brain or spinal cord injury; neurodegenerative disorders; Alzheimer, parkinsonian dementia or Huntington's disease; and convulsive disorders, such as epilepsy. They are also useful in the treatment of anxiety, schizofrenia, migraine, urinary incontinence, muscular spasms (spasticity); as analgesics and as anaesthetics; and for preventing withdrawal symptoms from drugs and alcohol. These effects are demonstrable in tests in vitro or in vivo e.g. in mice, rats, dogs or monkeys. Said compounds can be administered to them orally or parenterally. The inhibitory effect on the NMDA-type excitatory amino acid receptors is determined in vitro by measuring the inhibition of the NMDA-evoked $^3$H-acetylcholine release from corpus striatum tissue of rat brain essentially as described by Lehmann and Scatton, Brain Research, 252, 77 (1982). The inhibition of the NMDA-evoked $^3$H-acetylcholine release from striatal tissue slices is expressed as % of release of $^3$H-acetylcholine in response to stimulation with 50 μM NMDA compared to control.

The inhibitory effect on the NMDA-type excitatory amino acid receptors is determined also by an in vitro assay that measures the inhibition of binding of $^3$H-CGS 19755 to brain tissue preparations essentially according to Lehmann et al., J. Pharmacol. Exptl. Therap., 246, 65 (1988).

The anticonvulsive effect of the compounds of the invention is determined in vivo by inhibition of electroshock- or NMDA-induced convulsions in the mouse essentially as described in the last mentioned reference.

The analgetic effect of said compounds is determined in the rat and the mouse by intrathecal injection essentially according to Cahusac et al., Neuropharmacology, 23, 719 (1984).

I claim:

1. A compound of formula (I)

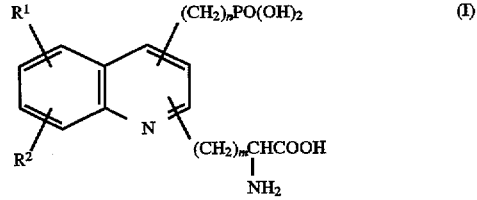

in which m is 0, 1 or 2;

n is 1, 2 or 3;

R$^1$ and R$^2$ are, independently and being the same or different, hydrogen, C$_1$–C$_7$ alkyl, C$_2$–C$_7$ alkenyl, C$_4$–C$_7$ alkadienyl, C$_6$ aryl, C$_6$ aryl-C$_1$–C$_7$ alkyl, C$_1$–C$_7$ alkoxy, C$_1$–C$_7$ alkanoyl, C$_1$–C$_7$ alkanoyloxy, C$_6$ aroyl, $C_6$ aroyloxy, $C_6$ aryl-$C_1$-$C_7$ alkanoyl, $C_1$-$C_7$ alkoxycarbonyl, $C_6$ aryl-$C_1$-$C_7$ alkoxycarbonyl, $C_1$-$C_7$ alkylthio, trifluoromethyl, trifluoromethoxy, $C_1$-$C_7$ alkylsulfonylamino, $C_1$-$C_7$ alkylamino, $C_1$-$C_7$ alkanoylamino, nitro, halogen, or $R^1$ and $R^2$ are, taken together, $C_1$-$C_7$ alkylene, $C_2$-$C_7$ alkenylene or $C_4$-$C_7$ alkadienylene, and pharmaceutically acceptable esters and salts, including hydrates, thereof.

2. A compound according to claim 1, wherein said compound has the formula:

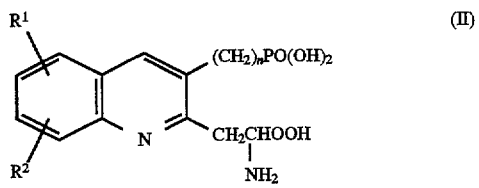

and wherein $R^1$ and $R^2$ are as defined in claim 1.

3. A compound of formula (I)

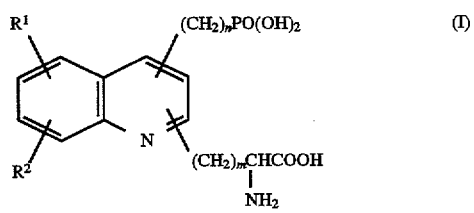

in which m is 0, 1 or 2;

n is 1, 2 or 3;

$R^1$ and $R^2$ are, independently and being the same or different, $C_1$-$C_4$ alkyl, $C_2$-$C_4$ alkenyl, $C_4$-$C_6$ alkadienyl, unsubstituted phenyl, phenyl substituted by one to three substituents selected from the group consisting of: $C_1$-$C_7$ alkyl, $C_1$-$C_7$ alkoxy, trifluoromethyl and halogen, pyridyl, $C_6$aryl-$C_1$-$C_4$-alkyl, $C_1$-$C_4$ alkoxy, $C_2$-$C_7$ alkanoyl, $C_2$-$C_5$ alkanoyloxy, benzoyl, benzoyl substituted by one to three substituents selected from the group consisting of: $C_1$-$C_7$ alkyl, $C_1$-$C_7$ alkoxy, trifluoromethyl and halogen, pyridylcarbonyl, benzoyloxy, benzoyloxy substituted on the phenyl ring by $C_1$-$C_7$ alkyl, halogen, $C_1$-$C_7$ alkoxy, or nicotinoyloxy, fluorine, chlorine, trifluoromethyl, $C_1$-$C_4$ alkanoylamino, $C_1$-$C_4$ alkylamino, $C_6$ aryl-$C_1$-$C_4$-alkanoyl, $C_1$-$C_4$ alkoxylcarbonyl or $C_6$ aryl-$C_1$-$C_4$ alkoxylcarbonyl, or $R^1$ and $R^2$ are when taken together, $C_2$-$C_6$ alkylene, $C_2$-$C_6$ alkenylene, $C_4$-$C_6$ alkadienylene.

4. A compound according to claim 1, wherein m is 1 and n is 1.

5. A compound according to claim 1, wherein said compound is in the form of a substantially pure enantiomer.

6. A compound according to claim 5, wherein said enantiomer is the (R)-isomer.

7. A compound according to claim 1, wherein said compound is in the form of a salt of an alkali metal, alkaline earth metal or a salt of ammonia or an organic amine.

8. A compound according to claim 1, wherein said compound is in the form of an ester selected from the group consisting of: $C_1$-$C_7$ alkyl, $C_6$ aryl-$C_1$-$C_7$ alkyl, $C_1$-$C_7$ alkanoyloxymethyl, $C_1$-$C_7$ alkylamino-straight chain $C_2$-$C_4$ alkyl.

9. A compound according to claim 8, wherein said ester is 2-diethyl-aminoethyl.

10. A compound according to claim 1, wherein said compound is selected from the group consisting of:

α-amino-3-(phosphonomethyl)-2-quinolinepropanoic acid;

α-amino-2-(phosphonomethyl)-3-quinolinepropanoic acid;

α-amino-6-chloro-3-(phosphonomethyl)-2-quinolinepropanoic acid;

(R)-α-amino-7-ethoxy-3-(phosphonomethyl)-2-quinolinepropanoic acid;

(R)-α-amino-6,7-dimethyl-3-(phosphonomethyl)-2-quinolinepropanoic acid;

(R)-α-amino-7-chloro-3-(phosphonomethyl)-2-quinolinepropanoic acid;

α-amino-6,7-dimethoxy-3-(phosphonomethyl)-2-quinolinepropanoic acid;

(R)-α-amino-7-methyl-3-(phosphonomethyl)-2-quinolinepropanoic acid hydrochloride;

(R)-α-amino-6,7-dichloro-3-(phosphonomethyl)-2-quinolinepropanoic acid;

(R)-α-amino-5-chloro-3-(phosphonomethyl)-2-quinolinepropanoic acid;

(R)-α-amino-6-fluoro-3-(phosphonomethyl)-2-quinolinepropanoic acid;

(R)-α-amino-6,8-dichloro-3-(phosphonomethyl)-2-quinolinepropanoic acid;

(R)-α-amino-7-chloro-6-methyl-3-(phosphonomethyl)-2-quinolinepropanoicacid;

(R)-α-amino-6,7-diethyl-3-(phosphonomethyl)-2-quinolinepropanoic acid;

(S)-α-amino-6,7-dimethyl-3-(phosphonomethyl)-2-quinolinepropanoic acid;

ethyl (R)-α-amino-6,7-dimethyl-3-(phosphonomethyl)-2-quinolinepropionate acid.

11. A compound according to claim 1, wherein said compound is:

(R)-α-Amino-6,7-dimethyl-3-(phosphonomethyl-2-quinolinepropanoic acid.

12. A compound according to claim 1, wherein said compound is:

(R)-α-amino-6,7-dichloro-3-(phosphonomethyl)-2-quinolinepropanoic acid.

13. A compound according to claim 1, wherein said compound is:

(R)-α-amino-6,7-diethyl-3-(phosphonomethyl)-2-quinolinepropanoic acid.

14. A process for the preparation of a compound of formula (I), according to claim 1, comprising:

a) reacting with a glycine anion equivalent in which amino and carboxylic acid moieties have protecting groups that prevent their entering into reaction, a compound of formula (VI):

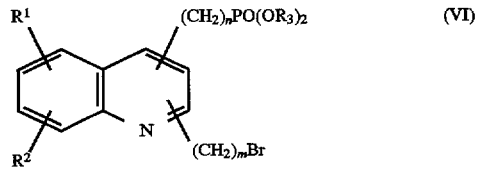

in which $R_3$ is $C_1$-$C_7$ alkyl, $C_6$ aryl or $C_6$ aryl $C_1$-$C_7$ alkyl; and b) removing said protecting groups from the product of step a) to produce said compound of formula I.

15. A process for the preparation of a compound of formula (I), according to claim 1, comprising:

a) reacting with a trialkyl phosphite, a compound of formula (VII):

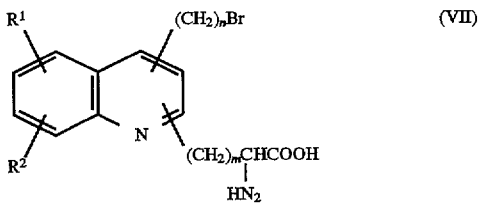

in which the amino and the carboxylic acid groups of said compound of formula (VII) have protecting groups that prevent their entering into reaction; and b) removing said protecting groups from the product of step a) to produce said compound of formula I.

16. A process for the preparation of a compound of formula (I), according to claim 1, comprising:
   a) reacting with a 2-amidoacrylate having protecting groups to prevent reaction, a compound of formula (VIII):

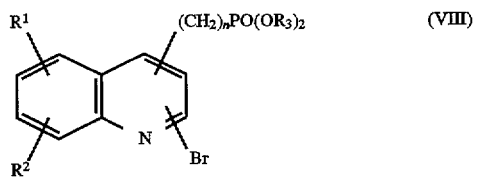

b) hydrogenating the compound formed in step a); and
   c) removing said protecting groups from the compound formed in step b).

17. A process for the preparation of a compound of formula (I), according to claim 1, comprising:
   a) reacting with a metallated β-iodoalanine having protecting groups to prevent reaction, a compound of formula (VIII):
   b) removing said protecting groups.

18. A pharmaceutical composition, comprising a compound of formula (I), according to claim 1, as an active ingredient together with a pharmaceutically acceptable carrier.

19. A pharmaceutical composition according to claim 18, wherein said active ingredient is a salt of said compound.

20. A pharmaceutical composition according to claim 18, wherein said active ingredient is an ester of said compound.

21. A pharmaceutical composition according to claim 18, wherein said active ingredient is a hydrate of said compound.

22. A pharmaceutical composition according to claim 18, wherein said active ingredient is an enantiomer of said compound.

23. A pharmaceutical composition according to claim 18, wherein said active ingredient is the (R)-enantiomer of said compound.

24. A method for the treatment of a subject suffering from overstimulation of excitatory amino acid receptors of the nervous system, comprising: administering an effective amount of a compound according to claim 1 to said subject.

25. A method for the treatment of pain in a subject in need of such treatment, comprising:
   administering an effective amount of a compound according to claim 1 to said subject.

26. A method for the treatment of ischemic conditions in a subject in need of such treatment, comprising: administering an effective amount of a compound according to claim 1 to said subject.

27. The method of claim 26, wherein said ischemic condition is the result of a stroke.

28. The method of claim 26, wherein said ischemic condition is the result of brain or spinal cord injury.

29. A method for the treatment of neurodegenerative disorders in a subject in need of such treatment, comprising: administering an effective amount of a compound according to claim 1 to said subject.

30. The method of claim 29, wherein said neurodegenerative disorder is Alzheimer's disease.

31. The method of claim 29, wherein said neurodegenerative disorder is Parkinsonian dementia.

32. The method of claim 29, wherein said neurodegenerative disorder is Huntington's disease.

33. A method for the treatment of convulsive disorders in a subject in need of such treatment, comprising: administering an effective amount of a compound according to claim 1 to said subject.

34. The method of claim 33, wherein said convulsive disorder is epilepsy.

35. A method for the treatment of anxiety in a subject in need of such treatment, comprising: administering an effective amount of a compound according to claim 1 to said subject.

36. A method for the treatment of schizophrenia in a subject in need of such treatment, comprising: administering an effective amount of a compound according to claim 1 to said subject.

37. A method for the treatment of migraine in a subject in need of such treatment, comprising: administering an effective amount of a compound according to claim 1 to said subject.

38. A method for the treatment of urinary incontinence in a subject in need of such treatment, comprising: administering an effective amount of a compound according to claim 1 to said subject.

39. A method for the treatment of muscular spasms in a subject in need of such treatment, comprising: administering an effective amount of a compound according to claim 1 to said subject.

40. A method for the treatment of hearing loss in a subject in need of such treatment, comprising: administering an effective amount of a compound according to claim 1 to said subject.

41. A method for the treatment of motor neuron diseases in a subject in need of such treatment, comprising: administering an effective amount of a compound according to claim 1 to said subject.

42. A method for the treatment of trauma from infections in a subject in need of such treatment, comprising: administering an effective amount of a compound according to claim 1 to said subject.

43. A method for preventing withdrawal symptoms from drugs or alcohol in a subject in need of such treatment or prevention, comprising: administering an effective amount of a compound according to claim 1 to said subject.

* * * * *